(12) United States Patent
Maiden

(10) Patent No.: US 10,466,184 B2
(45) Date of Patent: Nov. 5, 2019

(54) PROVIDING IMAGE DATA

(71) Applicant: PHASE FOCUS LIMITED, Sheffield South Yorkshire (GB)

(72) Inventor: Andrew Maiden, Sheffield (GB)

(73) Assignee: PHASE FOCUS LIMITED, Sheffield, South Yorkshire (GB)

(*) Notice: Subject to any disclaimer, the term of this patent is extended or adjusted under 35 U.S.C. 154(b) by 0 days.

(21) Appl. No.: 14/398,391

(22) PCT Filed: May 3, 2013

(86) PCT No.: PCT/GB2013/051168
§ 371 (c)(1),
(2) Date: Oct. 31, 2014

(87) PCT Pub. No.: WO2013/164645
PCT Pub. Date: Nov. 7, 2013

(65) Prior Publication Data
US 2015/0108352 A1    Apr. 23, 2015

(30) Foreign Application Priority Data

May 3, 2012    (GB) .................................. 1207800.2

(51) Int. Cl.
*G01N 23/20* (2018.01)
*G06T 11/00* (2006.01)

(52) U.S. Cl.
CPC ............ *G01N 23/20* (2013.01); *G06T 11/003* (2013.01)

(58) Field of Classification Search
CPC ...................................................... G01N 23/20

USPC .......................................................... 356/310
See application file for complete search history.

(56) References Cited

U.S. PATENT DOCUMENTS

| 3,556,639 | A | * | 1/1971 | Graser, Jr. | .......... G02B 27/4238 353/20 |
| 3,999,856 | A | | 12/1976 | Unterleitner | |
| 4,193,691 | A | * | 3/1980 | Fjarlie | ....................... G01J 3/04 349/201 |

(Continued)

FOREIGN PATENT DOCUMENTS

| CH | 101820817 A | 9/2010 |
| EP | 1832930 | 9/2007 |

(Continued)

OTHER PUBLICATIONS

International Preliminary Report on Patentability dated Jun. 13, 2013, International Application No. PCT/GB2011/052392 filed Dec. 2, 2011, pp. 1-7.

(Continued)

*Primary Examiner* — Kara E. Geisel
*Assistant Examiner* — Omar H Nixon
(74) *Attorney, Agent, or Firm* — MH2 Technology Law Group, LLP

(57) ABSTRACT

Embodiments of the present invention provide a method of providing image data for constructing an image of at least a region of a target object, comprising the steps of simultaneously recording, at a detector, a plurality of separable diffraction patterns formed by a respective portion of radiation scattered by the target object; and providing the image data via an iterative process responsive to the detected intensity of radiation.

31 Claims, 7 Drawing Sheets

(56) References Cited

U.S. PATENT DOCUMENTS

| | | | | |
|---|---|---|---|---|
| 4,549,204 | A * | 10/1985 | Bertero | G02B 21/0004 348/79 |
| 5,410,147 | A * | 4/1995 | Riza | G02F 1/21 250/214 LS |
| 5,570,180 | A * | 10/1996 | Nagai | G01J 3/02 356/310 |
| 5,889,593 | A * | 3/1999 | Bareket | G01B 11/0633 356/445 |
| 6,809,829 | B1 | 10/2004 | Takata et al. | |
| 6,809,845 | B1 | 10/2004 | Kim et al. | |
| 7,298,497 | B2 | 11/2007 | Millerd et al. | |
| 7,734,084 | B2 | 6/2010 | Stewart et al. | |
| 8,991,914 | B2 * | 3/2015 | Grovender | B63B 29/14 114/361 |
| 2003/0202634 | A1 | 10/2003 | Gerchberg | |
| 2004/0145747 | A1 | 7/2004 | Jasapara | |
| 2005/0274878 | A1 * | 12/2005 | Goldman | G01D 5/36 250/231.13 |
| 2005/0280813 | A1 * | 12/2005 | Jones | G01J 3/108 356/300 |
| 2006/0001864 | A1 * | 1/2006 | Kanzaki | G01N 21/94 356/237.2 |
| 2007/0252975 | A1 * | 11/2007 | Liang | G01B 11/254 356/124 |
| 2008/0048102 | A1 * | 2/2008 | Kurtz | H01L 31/0232 250/226 |
| 2008/0095312 | A1 | 4/2008 | Rodenburg et al. | |
| 2009/0016481 | A1 * | 1/2009 | Slinger | G01T 1/295 378/2 |
| 2009/0128641 | A1 * | 5/2009 | Ozluturk | H04N 5/23248 348/208.6 |
| 2009/0168158 | A1 * | 7/2009 | Schwertner | G02B 21/0024 359/385 |
| 2010/0135534 | A1 | 6/2010 | Weston et al. | |
| 2010/0165355 | A1 | 7/2010 | Kato | |
| 2010/0190115 | A1 * | 7/2010 | Kato | G03F 7/706 430/325 |
| 2010/0241396 | A1 * | 9/2010 | Rodenburg | A61B 6/483 702/167 |
| 2011/0292379 | A1 | 1/2011 | Kato | |
| 2011/0085173 | A1 | 4/2011 | Waller et al. | |
| 2011/0011608 | A1 | 5/2011 | Sugimoto | |
| 2011/0134438 | A1 | 6/2011 | Kato | |
| 2011/0157599 | A1 * | 6/2011 | Weaver | G01D 5/266 356/496 |
| 2011/0235863 | A1 * | 9/2011 | Maiden | G01T 1/00 382/103 |
| 2012/0179425 | A1 | 7/2012 | Zhang | |
| 2013/0033703 | A1 | 2/2013 | Humphry et al. | |
| 2013/0092816 | A1 | 4/2013 | Barrett et al. | |
| 2013/0181990 | A1 | 7/2013 | Rodenburg et al. | |

FOREIGN PATENT DOCUMENTS

| | | |
|---|---|---|
| EP | 2063260 | 5/2009 |
| EP | 2233905 | 9/2010 |
| GB | 2403616 A | 1/2005 |
| GB | 2481589 | 1/2012 |
| JP | 2005106835 | 4/2005 |
| JP | 2006-314643 A | 11/2006 |
| JP | 2007-526069 A | 9/2007 |
| JP | 2007-534956 A | 11/2007 |
| JP | 2010-528764 A | 8/2010 |
| JP | 2010-204755 A | 9/2010 |
| JP | 2012-511147 A | 5/2012 |
| WO | 96/38722 A1 | 12/1996 |
| WO | 2004/113856 A1 | 12/2004 |
| WO | 2005/106531 A1 | 11/2005 |
| WO | 2010/035033 A1 | 4/2010 |
| WO | 2010/064051 A1 | 6/2010 |
| WO | 2010/119278 A1 | 10/2010 |
| WO | 2011/033287 A1 | 3/2011 |
| WO | 2011/131981 | 10/2011 |
| WO | 2011/149000 | 12/2011 |

OTHER PUBLICATIONS

International Search Report dated Jun. 13, 2012, International Application No. PCT/GB2011/052392 filed Dec. 2, 2011, pp. 1-5.
Intellectual Property Office Search Report dated Apr. 11, 2011, United Kingdom Application No. GB1020516.9, pp. 1-4.
H. M. L. Faulkner et al., "Error tolerance of an iterative phase retrieval algorithm for movable illumination microscopy", Ultramicroscopy, vol. 103, 2005, pp. 153-164.
Andrew M. Maiden et al., "Superresolution imaging via ptychography", Journal of the Optical Society of America A, vol. 28, No. 4, Apr. 2011, pp. 604-612.
R. W. Gerchberg, "Super-resolution through error energy reduction", Optica ACTA, vol. 21, No. 9, Jan. 1974, pp. 709-720.
Manuel Guizar-Sicairos et al., "Phase retrieval with Fourier-weighted projections", Journal of the Optical Society of America A, vol. 25, No. 3, Mar. 2008, pp. 701-709.
Andrew M. Maiden et al., "An improved ptychographical phase retrieval algorithm for diffractive imaging", Ultramicroscopy, vol. 109, 2009, pp. 1256-1262.
Non-Final Office Action dated Jun. 18, 2015, U.S. Appl. No. 14/374,157, pp. 1-25.
Notification of Reasons for Refusal dated Jun. 11, 2015, Japanese Application No. 2013-541430, pp. 1-4 (including English Language Translation).
Non-Final Office Action dated Jul. 2, 2015, U.S. Appl. No. 14/114,086, pp. 1-35.
International Preliminary Report on Patentability dated Nov. 4, 2014 from International Application No. PCT/GB2013/051168 with Int'l Filing date May 3, 2013, pp. 1-9.
International Search Report dated Aug. 5, 2013, International Application No. PCT/GB2013/051168, pp. 1-3.
United Kingdom Search Report dated May 3, 2013, Great Britain Application No. GB1207800.2, pp. 1-7.
Martin Dierolf et al., "Ptychography & Lensless X-Ray Machine", Europhysics News, vol. 39, No. 1, 2008, pp. 22-24.
Oliver Bunk et al., "Influence of the Overlap Parameter on the Convergence of the Ptychographical Iterative Engine", Ultramicroscopy, vol. 108, 2008, pp. 481-487.
United Kingdom Search Report dated Aug. 11, 2011, Great Britain Application No. GB1107053.9, pp. 1-2.
Martin Dierolf et al., "Coherent laser scanning diffraction microscopy", Journal of Physics: Conference Series, vol. 186, 2009, pp. 1-3.
Andreas Menzel et al., "Advances in Ptychographical Coherent Diffractive Imaging", Proceedings of SPIE, vol. 7076, 2008, pp. 707609-01-707609-08.
Cameron M. Kewish et al., "Ptychographic characterization of the wavefield in the focus of reflective hard X-ray optics", Ultramicroscopy, vol. 110, 2010, pp. 325-329.
Pierre Thibault et al., "Probe retrieval in ptychographic coherent diffractive imaging", Ultramicroscopy, vol. 109, 2009, pp. 338-343.
International Search Report dated Aug. 17, 2012, International Application No. PCT/GB2012/050929 filed Apr. 27, 2012, pp. 1-4.
International Search Report and Written Opinion of the International Searching Authority dated Feb. 10, 2014, International Application No. PCT/GB2013/050155 filed Jan. 24, 2013, pp. 1-18.
D. Claus et al., "Ptychography: A novel phase retrieval technique, advantages and its application", Proceedings of SPIE, vol. 8001, 2011, pp. 800109-1-800109-6.
Richard M. Goldstein et al., "Satellite radar interferometry: Two-dimensional phase unwrapping", Radio Science, vol. 23, No. 4, 1988, pp. 713-720.
United Kingdom Search Report dated May 30, 2012, Great Britain Application No. GB1201140.9, pp. 1-5.
United Kingdom Search Report dated Oct. 3, 2012, Great Britain Application No. GB1201140.9, pp. 1-3.

(56) References Cited

OTHER PUBLICATIONS

Manuel Guizar-Sicairos et al., "Phase retrieval with transverse translation diversity: a nonlinear optimization approach", Optics Express, vol. 16, No. 10, 2008, pp. 7264-7278.
Written Opinion of the International Searching Authority dated Oct. 27, 2013, International Application No. PCT/GB2012/050929 filed Apr. 27, 2012, pp. 1-9.
First Office Action dated Mar. 3, 2016, Chinese Application No. 201280020664.3, pp. 1-8 (including English Language Summarization).
Japanese Office Action dated Feb. 16, 2016, Japanese Application No. 2014-506932, pp. 1-6 (including English Language Translation).
F. Hue et al., "Extended ptychography in the transmission electron microscope: Possibilities and limitations", Ultramicroscopy, vol. 111, 2011, pp. 1117-1123.
A. M. Maiden, "An annealing algorithm to correct positioning errors in ptychography", Ultramicroscopy, vol. 120, 2012, pp. 64-72.
PTO Non-Final Office Action dated Apr. 20, 2017, U.S. Appl. No. 15/001,887, pp. 1-49.

\* cited by examiner (a)

(b)

PROVIDING IMAGE DATA

CROSS-REFERENCE TO RELATED APPLICATIONS

This application is a U.S. National Stage application of PCT/GB2013/051168 filed May 3, 2013, which claims priority to Great Britain Application 1207800.2 filed May 3, 2012, the entire disclosures of which are hereby incorporated herein by reference in their entireties.

BACKGROUND

The present invention relates to methods and apparatus for providing image data from which an image of at least a portion of a target object may be generated. In particular, embodiments of the invention relate to methods and apparatus which reduce a time taken to record data for producing the image data.

WO 2005/106531, which is incorporated herein by reference for all purposes, discloses a method and apparatus of providing image data for constructing an image of a region of a target object. Incident radiation is provided from a radiation source at the target object. An intensity of radiation scattered by the target object is detected using at least one detector. The image data is provided responsive to the detected radiation. A method for providing such image data via an iterative process using a moveable softly varying or bandwidth limited probe function such as a transmittance function or illumination function is also disclosed. The methods and techniques disclosed in WO 2005/106531 are referred to as a ptychographical iterative engine (PIE).

PIE provides for the recovery of image data relating to at least an area of a target object from a set of diffraction pattern measurements. Several diffraction patterns are recorded at a measurement plane using one or more detectors, such as a CCD or the like. A probe function, which might be a transmittance function associated with a post-target object aperture or an illumination function, must be known or estimated.

WO 2010/064051, which is incorporated herein by reference for all purposes, discloses an enhanced PIE (ePIE) method wherein it is not necessary to know or estimate the probe function. Instead a process is disclosed in which the probe function is iteratively calculated step by step with a running estimate of the probe function being utilised to determine running estimates of an object function associated with a target object.

Other methods of providing image data based on measurement of scattered radiation are also known.

FIG. 1 illustrates an apparatus 100 suitable for use in the PIE and ePIE methods referred to above, and other coherent diffractive imagine techniques. The apparatus 100 is suitable to provide image data of an object which may, although not exclusively, be used to produce an image of at least a region of the object.

A radiation source, which although not shown in FIG. 1, is a source of radiation 10 which falls upon a focusing arrangement 20, such as one or more lenses, and is caused to illuminate a region of a target object 30. It is to be understood that the term radiation is to be broadly construed. The term radiation includes various wave fronts. Radiation includes energy from a radiation source. This will include electromagnetic radiation including X-rays, emitted particles such as electrons. Other types of radiation include acoustic radiation, such as sound waves. Such radiation may be represented by a wave function $\Psi(r)$. This wave function includes a real part and an imaginary part as will be understood by those skilled in the art. This may be represented by the wave function's modulus and phase. $\Psi(r)^*$ is the complex conjugate of $\Psi(r)$ and $\Psi(r)\Psi(r)^* = |\Psi(r)|2$ where $|\Psi(r)|2$ is an intensity which may be measured for the wave function.

The lens 20 forms a probe function P(r) which is arranged to select a region of the target object 30 for investigation. The probe function selects part of an object exit wave for analysis. P(r) is the complex stationary value of this wave field calculated at the plane of the object 30.

It will be understood that rather than weakly (or indeed strongly) focusing illumination on the target object 30, unfocused radiation can be used with a post target aperture. An aperture is located post target object to thereby select a region of the target 30 for investigation. The aperture is formed in a mask so that the aperture defines a "support". A support is an area of a function where that function is not zero. In other words, outside the support, the function is zero. Outside the support the mask blocks the transmittance of radiation. The term aperture describes a localised transmission function of radiation. This may be represented by a complex variable in two dimensions having a modulus value between 0 and 1. An example is a mask having a physical aperture region of varying transmittance.

Incident radiation 10 thus falls upon the up-stream side of the target object 30 and is scattered by the target object 30 as it is transmitted. The target object 30 should be at least partially transparent to incident radiation. The target object 30 may or may not have some repetitive structure. Alternatively the target object 30 may be wholly or partially reflective in which case a scattering pattern is measured based on reflected radiation.

A specimen wave O(r) is thus formed as an exit wave function of radiation after interaction with the object 30. In this way O(r) represents a two-dimensional complex function so that each point in O(r), where r is a two-dimensional coordinate, has associated with it a complex number. O(r) will physically represent an exit wave that would emanate from the object which is illuminated by a plane wave. For example, in the case of electron scattering, O(r) would represent the phase and amplitude alteration introduced into an incident wave as a result of passing through the object 30 of interest. The probe function P(r) (or transmission function) selects a part of the object exit wave function for analysis. It will be understood that rather than selecting an aperture a transmission grating or other such filtering function may be located downstream of the object function. The probe function P(r-R) is an aperture transmission function where an aperture is at a position R. The probe function can be represented as a complex function with its complex value given by a modulus and phase which represent the modulus and phase alterations introduced by the probe into a perfect plane wave incident up it.

An exit wave function $\psi(r,R)$ is an exit wave function of radiation 35 as it exits the object 30. This exit wave $\psi(r,R)$ forms a diffraction pattern $\Psi(u)$ at a diffraction plane. Here r is a vector coordinate in real space and u is a vector coordinate in diffraction space.

In order to select the region of the target object 30 to be illuminated or probed, the lens(es) 20 or aperture may be mounted upon an x/y translation stage which enables movement of the probe function with respect to the object 30. It will also be realised that the object 30 may be moved with respect to the lens(es) or aperture.

A detector 40 is a suitable recording device such as a CCD camera or the like which allows the diffraction pattern to be recorded. The detector 40 allows the detection of the diffraction pattern in the diffraction plane. The detector 40 may comprise an array of detector elements, such as in a CCD.

As will be appreciated, in order to produce image data corresponding to the target object, such as the object function O(r), a plurality of diffraction patterns are recorded at corresponding, partly overlapping, probe positions.

It is an object of embodiments of the invention to at least mitigate one or more of the problems of the prior art.

SUMMARY OF THE INVENTION

According to an aspect of the present invention there is provided method of providing image data for constructing an image of at least a region of a target object, comprising the steps of simultaneously recording, at a detector, a plurality of separable diffraction patterns formed by a respective portion of radiation scattered by the target object; and providing the image data via an iterative process responsive to the detected intensity of radiation.

Radiation incident upon the target object may be substantially coherent. In some embodiments a plurality of beams of radiation incident upon the target object are substantially mutually coherent. In embodiments of the invention the iterative method is based upon the plurality of diffraction patterns, wherein each diffraction pattern corresponds to a respective probe position. The method may be a coherent diffractive imaging method. In some embodiments the image data is based on more than one plurality of diffraction patterns wherein the group of all diffraction patterns comprises partially overlapping adjacent diffraction patterns. That is, adjacent diffraction patterns in the group partially overlap. The overlap may be in range 50-90%. The overlap may be an overlap in radiation responsible for each respective diffraction pattern upon the object. The diffraction patterns recorded simultaneously may not overlap, but may be substantially separate. However a totality of all recorded diffraction patterns recorded using a plurality of different positions of an aperture array may comprise overlapping diffraction patterns.

It will be appreciated that the image data does not necessarily have to be used for generating an image. The image data may merely be indicative of the target object and used for another purpose rather than generating an image, for example as a process control input, or to output one or more values derived from some or all of the image data.

According to an aspect of the present invention there is provided a method of providing image data for constructing an image of a region of a target object, comprising the steps of:
  simultaneously recording at a detector a plurality of diffraction patterns formed by radiation scattered by the target object;
  providing the image data via a process responsive to the detected intensity of radiation.

In some embodiments, radiation incident upon the target object comprises a plurality of portions each forming a respective diffraction pattern at the detector. The wavefront comprising the plurality of portions may be formed by being incident upon an aperture array. A lens may be provided to cause each of the plurality of portions to be divergent.

In some embodiments, an exit wave emanating from the target object may be incident upon an aperture array to select a plurality of regions of the exit wave to each form one of the diffraction patterns at the detector. In some embodiments, the method may comprise moving the aperture array amongst a plurality of positions.

The aperture array may be arranged such that zero order regions of each diffraction pattern are spatially separated at the plane of the detector.

Each of the diffraction patterns may correspond to a probe function.

According to an aspect of the present invention there is provided an apparatus for determining image data for constructing an image of a region of a target object, comprising:
  a detector for recording an intensity of radiation falling thereon;
  a processor for determining the image data based upon data received from the detector, wherein the processor is arranged to determine the image data based upon a plurality of diffraction patterns simultaneously recorded by the detector.

BRIEF DESCRIPTION OF THE DRAWINGS

Embodiments of the invention will now be described by way of example only, with reference to the accompanying figures, in which.

DETAILED DESCRIPTION OF EMBODIMENTS OF THE INVENTION

In embodiments of the invention a plurality of diffraction patterns are simultaneously recorded by a detector. Image data is determined based, at least in part, upon the plurality of diffraction patterns. Advantageously, this reduces a time required to record data sufficient for the determination of the image data.

Figure 1:
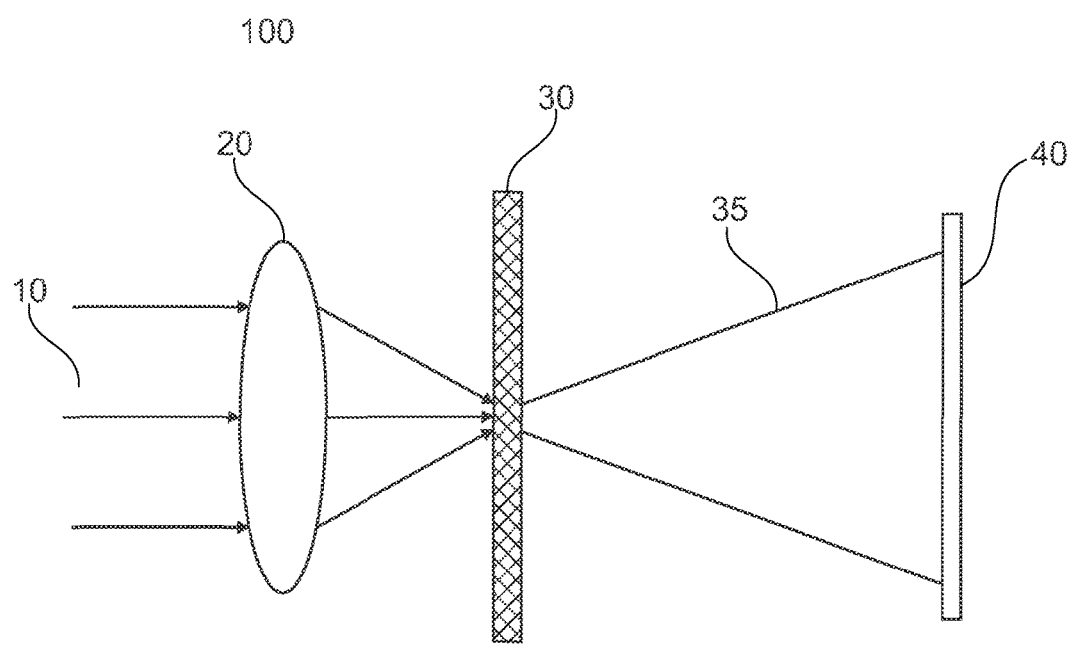
FIG. 1 shows an apparatus 100 suitable for use in the PIE and ePIE methods.
Figure 2:
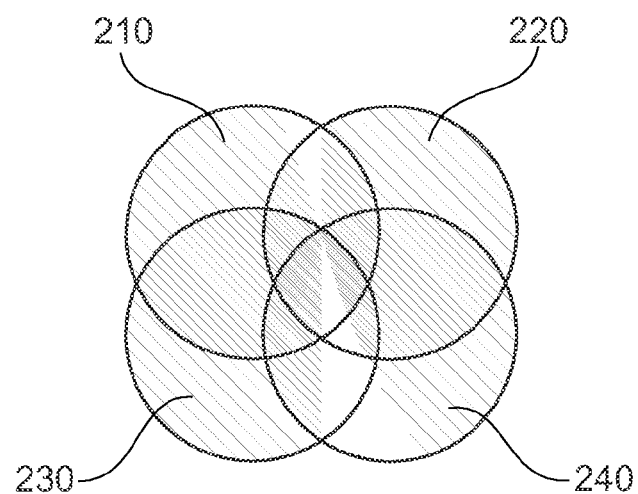
FIG. 2 shows an arrangement according to an embodiment of the invention.
Figure 2:
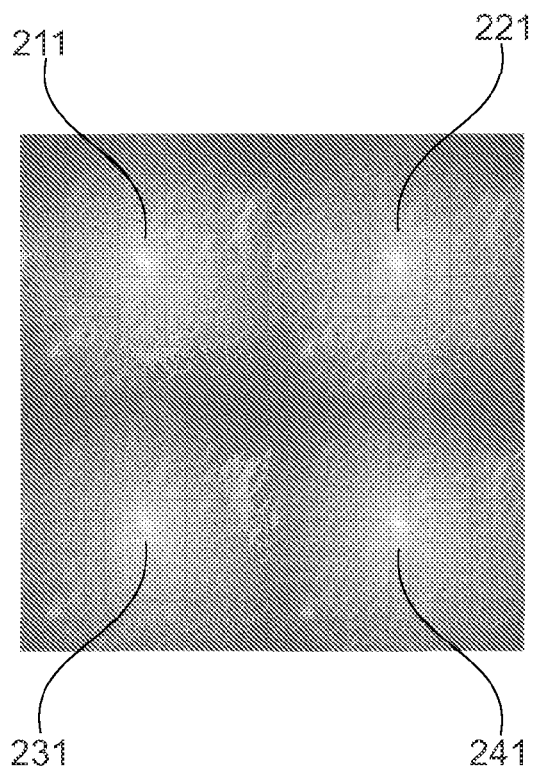

FIG. 2 illustrates a wavefront at a sample plane in FIG. 2(a) and at a detector plane in FIG. 2(b) according to an embodiment of the invention.

Referring to FIG. 2(a) the wavefront at the sample plane (the plane of the object) is arranged to simultaneously form a plurality of probe functions at different respective positions. In the example shown in FIG. 2(a) the wavefront is arranged to form four probe functions, however it will be realised that this number is merely an example and that other numbers of probe functions may be chosen. The wavefront illustrated in FIG. 2(a) is arranged to form first 210, second 220, third 230 and fourth 240 probe functions which select corresponding regions of a target object.

FIG. 2(b) illustrates diffraction patterns recorded by a detector corresponding to the wavefront shown in FIG. 2(a). In some embodiments of the invention at the plane of the target object, the portions of the wavefront corresponding to each probe function are arranged to be partially overlapping and divergent from one-another. The divergent nature of the portions of the wavefront causes the formation of diffraction patterns at the plane of the detector which have a further degree of separation than at the plane of the object. In particular, the portions of the wavefronts have diverged sufficiently that zero-orders (the bright spots shown in FIG. 2(b)) of each diffraction pattern are spatially separated. It will be realised that embodiments of the invention may be envisaged in which the portions of the wavefront corresponding to the plurality of probe functions are not divergent at the object plane.

The detector is able to record the plurality of diffraction patterns in a single exposure. In some embodiments, the image data may be determined based upon the intensity of radiation measured in a single exposure i.e. all diffraction patterns are recorded in the single exposure, whilst in other embodiments the plurality of diffraction patterns recorded in one exposure may be combined with a further plurality of diffraction patterns recorded in one or more subsequent exposures.

Figure 3:
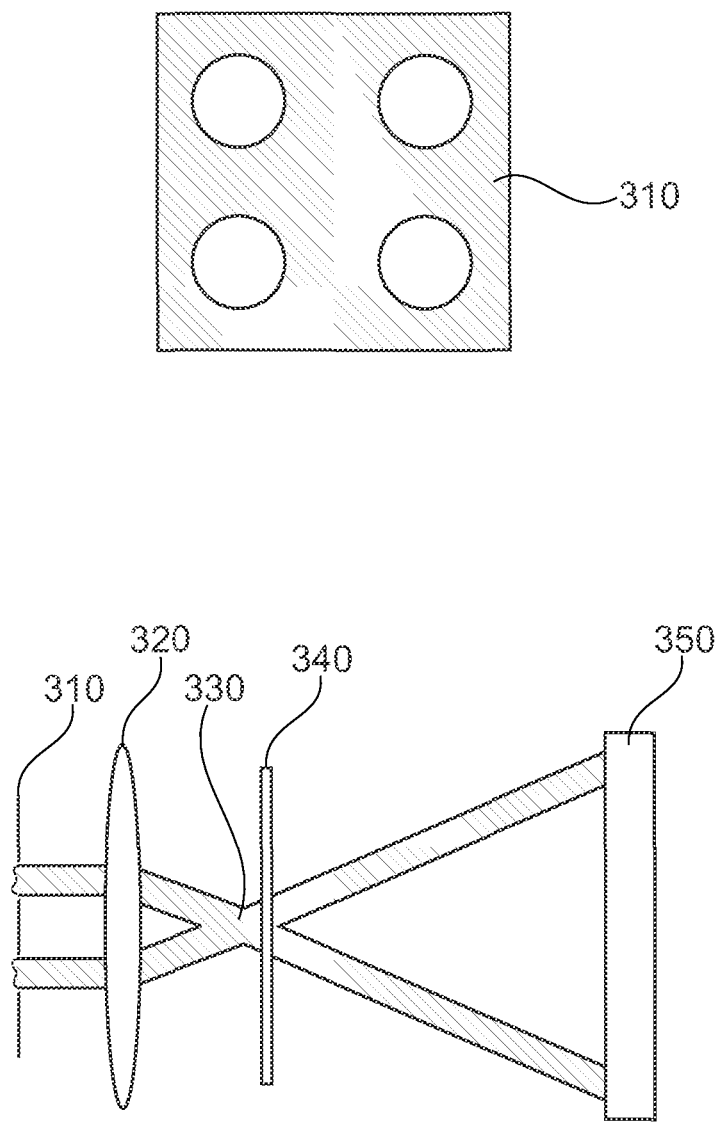
FIG. 3 shows an apparatus according to an embodiment of the invention.

FIG. 3 illustrates an apparatus 300 according to an embodiment of the invention. The apparatus comprises an aperture array 310, a lens and a detector 350. Also illustrated in FIG. 3 is a focus plane 330 and an object 340.

The aperture array 310 is a mask having a plurality of apertures formed therein. The mask is formed from material capable of substantially blocking incident radiation. The plurality of apertures are arranged such that radiation incident on the mask passes through the apertures to form a wavefront having corresponding probe function portions. The wavefront emanating from the aperture array 310 is directed toward a lens 320 to focus radiation toward the object 340. As shown in FIG. 3, a focal plane 330 of the lens 320 is arranged to be upstream (prior to) of the object 340. This causes the portions of the wavefront corresponding to each probe function to diverge downstream of the focal plane 330. The wavefront interacts with the object 340 and is at least partly transmitted through the object 340. In other embodiments, the object may be reflective and the wavefront may be at least partially reflected by the object 340. The detector 350 is arranged to simultaneously record an exit wave from the object which includes portions corresponding to the plurality of probe functions. Based on these portions a process may be performed as described in the PIE and ePIE references, as well as other process which are known to the skilled person, to provide image data based on the measured intensity of the diffraction patterns.

Embodiments of the invention may also be envisaged in which a post target aperture array 310 is used. In these embodiments radiation impinging upon the target object 340 forms an exit wave and the aperture array 310 is arranged downstream of the target object 340 such that portions of the exit wave corresponding to each aperture form respective probe functions. As the radiation incident upon the target object 340 is not divergent, the apertures in the aperture array 310 do not overlap. In order to provide a degree of overlap of probe functions necessary for a phase retrieval algorithm, the aperture array is moved between a plurality of positions to achieve overlap between probe positions. The aperture array 310 may be moved by, for example, an x, y translation stage.

Figure 4:
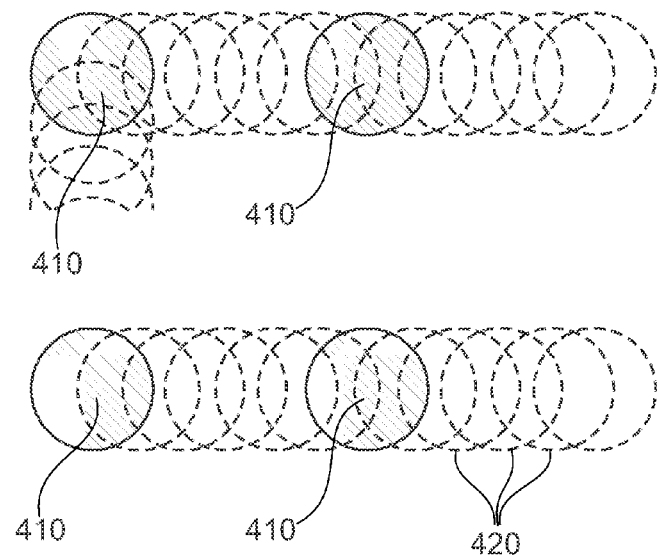
FIG. 4 shows an apparatus according to an embodiment of the invention.

FIG. 4 illustrates probe positions according to an embodiment of the invention. A first plurality of probe positions 410 corresponds to those in the aperture array 310 with the array 310 at a single location. The aperture array 310 may be moved in one or both of x and y directions such that the detector 350 records diffraction patterns at one or more further locations such that probe positions overlap. Some of the further probe positions 420 are indicated in FIG. 4. It will be realised that the number of aperture array locations and number of apertures present in the array 310 is merely illustrative.

A process may be performed as described in the PIE and ePIE references, as well as other process which are known to the skilled person, to provide image data based on the measured intensity of the plurality of diffraction patterns formed with the aperture array 310 at each of the plurality of locations.

Figure 5:
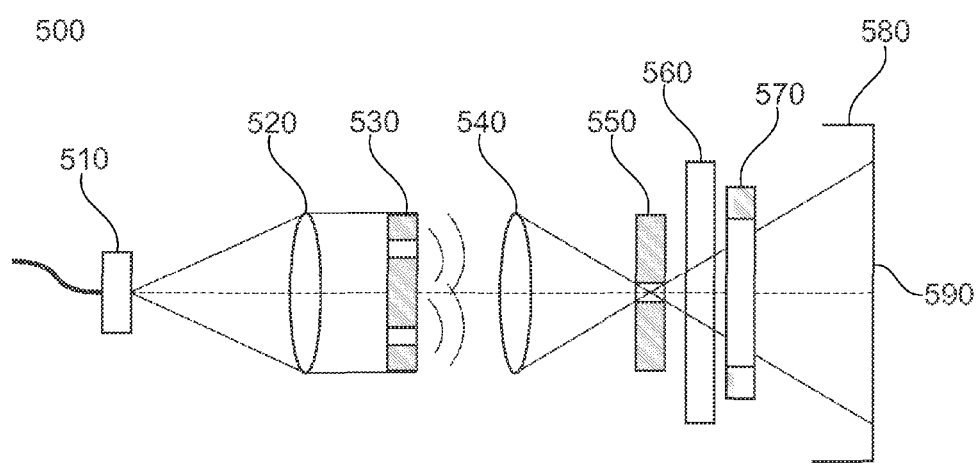
FIG. 5 shows an apparatus according to another embodiment of the invention.
Figure 6:
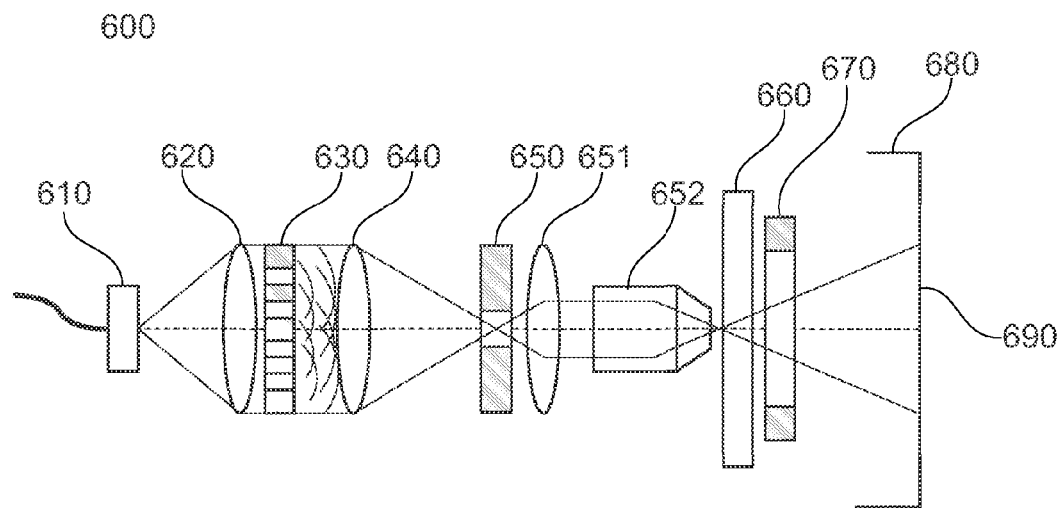
FIG. 6 shows an apparatus according to a further embodiment of the invention.

FIGS. 5 and 6 illustrate apparatus according to further embodiments of the invention.

FIG. 5 shows an apparatus 500 comprising a fibre optic connector 510 which is arranged to receive radiation in the form of light from a fibre optic cable. The connector 510 terminates a fibre optic cable to couple the cable to a laser output. It will be realised that the apparatus 500 may be used with other types of radiation other than light received from a fibre optic. A first lens 520 is arranged a distance $L_1$ from the connector 510 to collimate received light. The distance $L_1$ may be chosen to provide suitable a radiation beam width, such as 10 mm FWHM. This beam width may be equal to a spacing distance of apertures in an aperture array 530 so that each aperture receives substantially the same radiation intensity. The aperture array 530 is arranged a distance $L_2$ from the first lens 520. In some embodiments $L_2$ is equal to $L_1$. In the embodiment shown, the aperture array 530 is a 2×2 array providing four portions of radiation, although it will be realised that other numbers of aperture may be present in either dimension. A diameter of each aperture in the exemplary embodiment is 150 µm, although it will be realised that other diameters may be used. A second lens 540 may be arranged in an 2-f configuration with the aperture array 530 and a mask aperture 550. The second lens 540 is arranged a focal length $L_3$ from the aperture array 530 and a further focal length $L_4$ from the mask aperture 550 in some embodiments. The focal length in one exemplary embodiment is 50 mm, although it will be realised that other focal lengths may be used. The mask aperture comprises an aperture which may central in the mask. The aperture has a size which is less than an airy disc formed by the apertures in the aperture array at a plane of the mask aperture. The mask aperture may be 600 µm, although it will be realised that this is merely exemplary. A target object 560 is arranged downstream of the mask aperture 550 and is preceded, in some embodiments, by a diffuser which may be made of a plastic material. The presence and material of the diffuser 570 may be chosen appropriately. The diffuser 570 acts to reduce a dynamic range of signal at a detector 590. The apparatus further comprises a reflection mask 580. The reflection mask 580 is provided to prevent or reduce multiple reflections, such as between a glass slide supporting the object and the CCD. The reflection mask is arranged a distance $L_6$ from the sample. The distance $L_6$ is selected depending upon a diameter of the reflection mask 580. A larger diameter mask 580 enables a larger distance $L_6$, but is less effective at removing reflections. In one embodiment the reflection mask 580 has a diameter of 1 mm and $L_6$ is 2× the mask diameter i.e. 2 mm. In an exemplary embodiment the detector 590 is placed a distance $L_7$ away from the sample 560, which may be, for example, 33 mm. This distance ensures that the scattered light from each probe is isolated spatially at the detector 590. The target 560 is located a distance $L_5$ away from a focal plane of the second lens 540.

This distance $L_5$ ensures that the multiple probes have a sufficient overlap at the plane of the target. The focal plane of the second lens 540 may coincide with the plane of the mask aperture 550.

FIG. 6 illustrates an apparatus 600 according to an embodiment of the invention. The apparatus 600 comprises like parts to that described with reference to FIG. 5 and, except where necessary, a repetition thereof will be omitted.

The apparatus comprises an aperture array having 4×4 (16) apertures. Due to the greater number of apertures, the outer-most apertures in opposing corners have a greater spacing from each other than in the embodiment described with reference to FIG. 5. Therefore a spherical aberration of the radiation may be important to focussing the radiation. The second lens 640 is selected to have a greater focal length of, for example, 100 mm. The mask aperture 650 may be formed from an iris. The iris may have a minimum closed diameter of approximately 800 µm, although other diameters may be used. A third lens 651 is provided with a microscope objective lens 652 arranged in-between the mask aperture 650 and the target object 660, upstream of the target object 660. The third lens 651 may have a focal length of, for example, 35 mm and is arranged to form a de-magnified image of the aperture 530. A collimated image is formed when the third lens 651 is arranged spaced apart from a focal plane of the second lens 640 by its focal length e.g. 35 mm. In some arrangements the third lens 651 may be arranged closer than its focal length to the focal plane of the second lens 640 which results in a reduced numerical aperture of the microscope objective lens 652, for example due to space restrictions. The microscope objective lens 652 is arranged to focus the plurality of beams of radiation. The microscope objective lens may have a magnification ratio of 10× or 20×, although other ratios may be used. The target object 660 is arranged a distance $L_6$ from the focal plane of the objective lens 652. The distance $L_6$ determines a degree of overlap between probe positions. At $L_6=0$ the probe positions have 100% overlap. A desired degree of overlap is around 70%, although may be in the range of 80-60% or 90-50%. $L_6$ is therefore selected to obtain a desired overlap of probe positions. The distance may be, for example, 400 µm although other distances may be used. The detector 690 is located a distance $L_7$ from the target object which may be 20-30 mm to ensure sufficient spatial resolution of each of the 16 diffraction patterns. It will be realised that other distances may be used.

Some embodiments of the invention include a step of segmenting the detector 590, 690. The detector is segmented to isolate each diffraction pattern such that the simultaneously recorded diffraction patterns may be separately processed to determine the image data. *. A method according to an embodiment of the invention will be described with reference to FIG. 7.

In step 710 the detector is divided into a plurality of regions or segments. It will be realised that the division of the detector may be performed in software i.e. with no physical division of the detector. Instead the response of the detector to the impinging radiation is allocated amongst a plurality of "virtual" detectors, such as by being independently stored in memory in separate data structures. The segments may be equal sized. In an exemplary embodiment a detector having 1024 by 1024 pixels is divided into segments of 256 pixels by 256 pixels when the detector is arranged to simultaneously receive 16 diffraction patterns in a 4×4 arrangement.

In step 720 a centre of each diffraction pattern within the respective segment is determined. The centre of the diffraction pattern may be found by means of thresholding, edge detection and fitting the measured pattern to a circle. In this sense, thresholding is understood to mean that any pixel of the detector response below a threshold value is set to a predetermined value, for example 0.

In step 730 an average centre position for each diffraction pattern within the segments is determined based upon the plurality of centres determined in step 720. The average position may be a mean position determined from amongst the plurality of centres from step 720.

In step 740 each diffraction pattern is shifted, if necessary, so as to centre the pattern at the average centre position determined in step 730. The diffraction pattern may be padded with a predetermined value, such as 0, to allow for the movement of the measured data.

In step 750 each segment is cropped to its original size, if necessary. In step 760 any cross-talk between neighbouring segments may be removed. The removal of cross-talk may be performed by the application of a hamming or Gaussian window to each segment.

Figure 8:
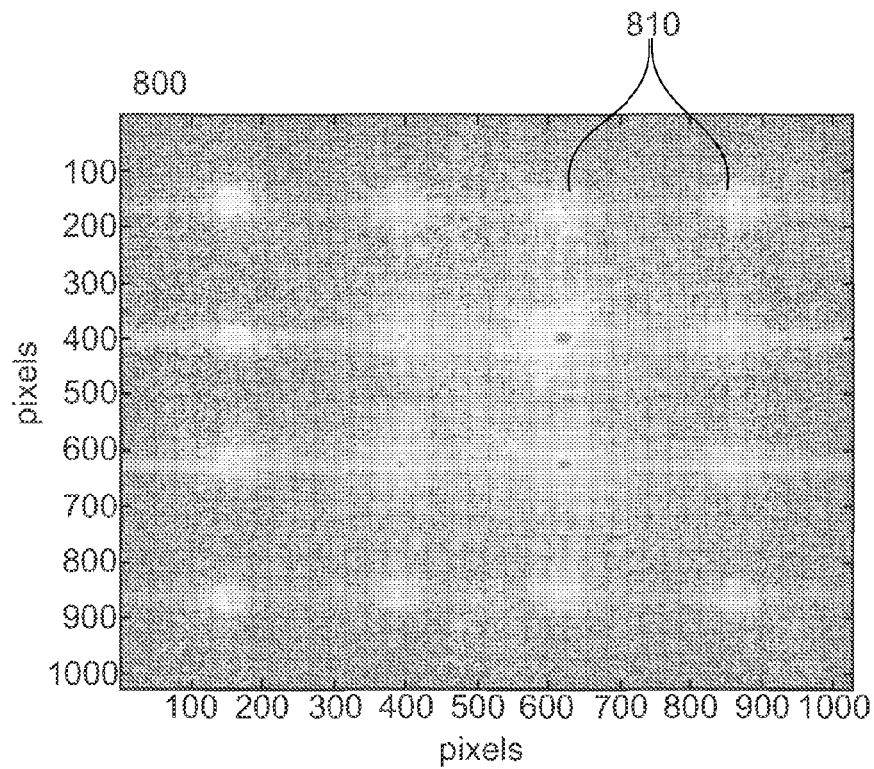
FIG. 8 illustrates a plurality of diffraction patterns according to an embodiment of the invention.

FIG. 8 illustrates data 800 output by a detector indicative of measured diffraction patterns 810 (only two of which are indicated) using a 4×4 aperture array which produces 16 simultaneously measured diffraction patterns.

Figure 7:
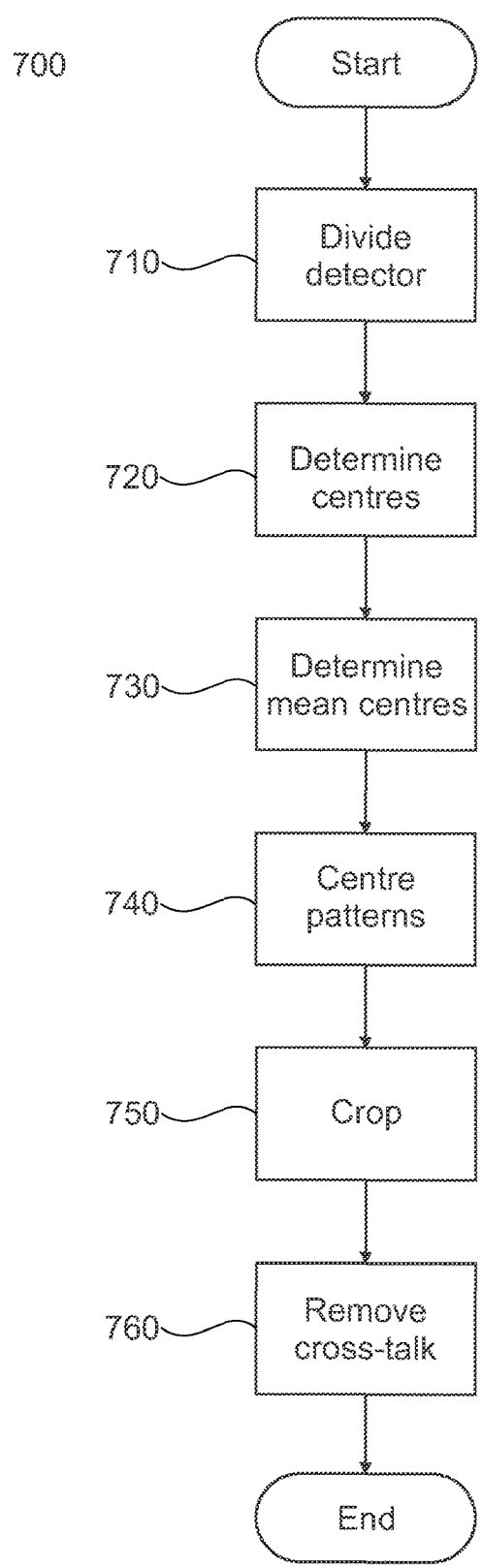
FIG. 7 shows a method according to an embodiment of the invention.
Figure 9:
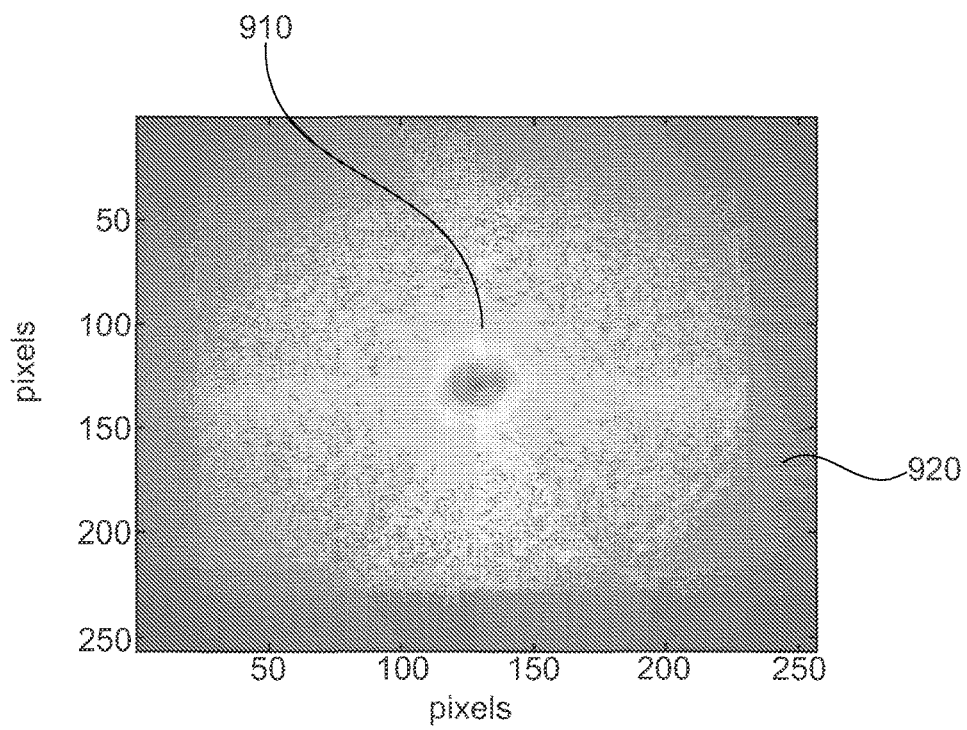
FIG. 9 illustrates a diffraction pattern separated according to an embodiment of the invention.

FIG. 9 illustrates a diffraction pattern 910 based on a portion of the data 800 shown in FIG. 8 following application of an embodiment of the method 700 described with reference to FIG. 7. As can be appreciated from a comparison of FIGS. 8 & 9, the detector response in FIG. 8 is 1024×1024 pixels, whereas the diffraction pattern for one diffraction patterns shown in FIG. 9 is 256×256 pixels. A border exists on the right and lower sides of the diffraction pattern 920. The border is as a result of centering the diffraction pattern before applying a Gaussian window. In this case the Gaussian window is generated by first forming an aperture of '1s' of a predetermined diameter, such as 210 pixels, and then smoothing the aperture edge with a Gaussian drop off with a predetermined width, such as 20 pixels. In another embodiment, the window is applied before shifting the diffraction pattern as in step 740, but whilst ensuring the centre of the window corresponds to the centre of the diffraction pattern.

In prior art methods, a position of a respective probe function corresponding to a measured diffraction pattern is known from movement of, for example, an aperture, focussing arrangement or the object. Embodiments of the invention comprise a method of determining a location of the probe position corresponding to a diffraction pattern. In a first step a distance between the plurality of diffraction patterns is determined. The distance may be determined based upon the average centre position of each diffraction pattern determined in step 730 of FIG. 7. The distance between diffraction patterns, at the plane of the detector, is determined based on the average centre location of the diffraction patterns. The distance may be converted from pixels to meters based on the dimensions of the detector pixels, as will be appreciated. The distance at the detector plane may be scaled using a ratio of the focal distance (distance between the object and the point of focus) to the camera length. The focal point may be determined using a back propagation of the probe from a prior reconstruction using, for example, ePIE.

Figure 10:
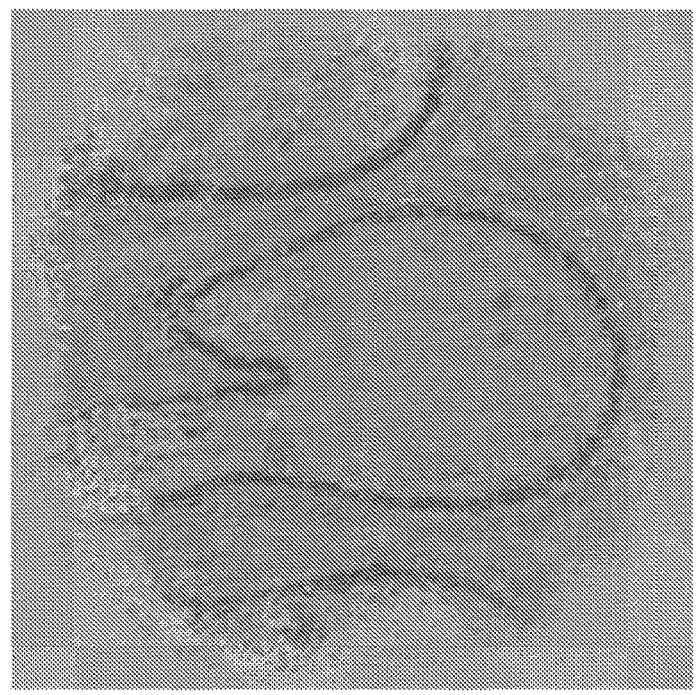
FIG. 10 illustrates an image produced from image data according to an embodiment of the invention.

FIG. 10 illustrates a representation of image data determined according to an embodiment of the invention using a plurality of simultaneously measured diffraction patterns. In the present case, the image data is based on use of a 2×2 aperture array i.e. 4 simultaneously recorded diffraction patterns. Embodiments of the invention allow image data to be determined based on a single exposure of the object to the radiation, a so called "single shot" method, wherein the method of determining the image data uses a plurality of diffraction patterns.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A method of providing image data for constructing an image of at least a region of a target object, comprising:
    forming a wavefront of radiation having a plurality of partially overlapping and divergent portions at a plane of the target object;
    simultaneously recording, at a detector, a plurality of diffraction patterns each formed by one of the portions of the radiation scattered by the target object, wherein the plurality of diffraction patterns are simultaneously received at the detector with each diffraction pattern being spatially separated at the detector; and
    providing the image data via an iterative process responsive to an intensity of the plurality of spatially separated diffraction patterns recorded at the detector, wherein the iterative process is arranged to iteratively update an estimate of at least one of a probe function indicative of at least a portion of the wavefront of radiation incident on the target object and an object function corresponding to the target object from a previous iteration of the iterative process.

2. The method of claim 1, wherein the respective portions of radiation are incident on the target object.

3. The method of claim 2, wherein the plurality of portions is formed by the radiation being incident upon an aperture array.

4. The method of claim 3, comprising moving the aperture array amongst a plurality of positions.

5. The method of claim 4, wherein the plurality of positions are arranged such that the portions of incident radiation at least partly overlap.

6. The method of claim 3, wherein the aperture array is arranged such that zero order regions of each diffraction pattern are spatially separated at a plane of the detector.

7. The method of claim 3, wherein the aperture array is arranged upstream of the target object.

8. The method of claim 3, wherein the aperture array comprises a plurality of apertures arranged in geometric pattern.

9. The method of claim 8, wherein the geometric pattern is a grid.

10. The method of claim 3, wherein the aperture array comprises one of four, six, eight, ten, twelve or sixteen apertures.

11. The method of claim 3 wherein the aperture array comprises a plurality of generally circular apertures.

12. The method of claim 2, comprising causing each of the plurality of portions of radiation to diverge by providing a lens.

13. The method of claim 12, wherein a focal plane of the lens is upstream of the object.

14. The method of claim 1, wherein an exit wave emanating from the target object is incident upon an aperture array to select a plurality of regions of the exit wave to each form one of the diffraction patterns at the detector.

15. The method of claim 1, comprising masking a periphery of the radiation prior to the radiation impinging on the object.

16. The method of claim 1, wherein each of the diffraction patterns corresponds to a probe function.

17. The method of claim 1, comprising dividing a response of the detector into a plurality of segments.

18. The method of claim 17, wherein each segment comprises a respective diffraction pattern.

19. The method of claim 1, wherein the iterative process is arranged to determine the image data based on each of the diffraction patterns recorded in a respective segment of the detector.

20. A non-transitory computer readable medium comprising computer readable instructions which, when executed by at least one electronic processor, perform a method according to claim 1.

21. An apparatus for determining image data for constructing an image of a region of a target object, comprising:
    a radiation focusing mechanism configured to form a wavefront of radiation having a plurality of partially overlapping and divergent portions at a plane of the target object;
    a detector for simultaneously recording an intensity of a plurality of diffraction patterns each formed by one of the respective portions of radiation scattered by the target object, wherein the plurality of diffraction patterns are simultaneously received at the detector with each diffraction pattern being spatially separated at the detector;

a processor for determining the image data based upon data received from the detector, wherein the processor is arranged to determine the image data based upon the plurality of spatially separated diffraction patterns simultaneously recorded by the detector according to an iterative process, wherein the iterative process is arranged to iteratively update an estimate of at least one of a probe function indicative of at least a portion of the wavefront of radiation incident on the target object and an object function corresponding to the target object from a previous iteration of the iterative process.

22. The apparatus of claim 21, wherein the radiation focusing mechanism comprises an aperture array arranged to cause the radiation falling on the detector to form the plurality of diffraction patterns.

23. The apparatus of claim 22, wherein the aperture array comprises a plurality of apertures arranged in geometric pattern.

24. The apparatus of claim 23, wherein the geometric pattern is a grid.

25. The apparatus of claim 22, wherein the aperture array is arranged upstream of the target object.

26. The apparatus of claim 22, wherein the radiation focusing mechanism comprises first and second lenses, the aperture array being arranged between the first and second lenses.

27. The apparatus of claim 26, wherein one or both of: the first lens is arranged to collimate received radiation, and the second lens is arranged to focus radiation received from the aperture array.

28. The apparatus of claim 26, wherein a focal plane of the second lens is upstream of the target object.

29. The apparatus of claim 26, comprising an aperture mask arranged generally at a focal plane of the second lens.

30. The apparatus of claim 21, wherein the processor is arranged to divide an output of the detector into a plurality of segments, each of the segments including data corresponding to one of the plurality of diffraction patterns.

31. The apparatus of claim 30, wherein the dividing comprises a step of removing cross-talk from amongst neighbouring segments.

* * * * *